March 19, 1974 G. H. MACK ET AL Plant Pat. 3,530
CHRYSANTHEMUM PLANT
Filed July 10, 1972 2 Sheets-Sheet 1
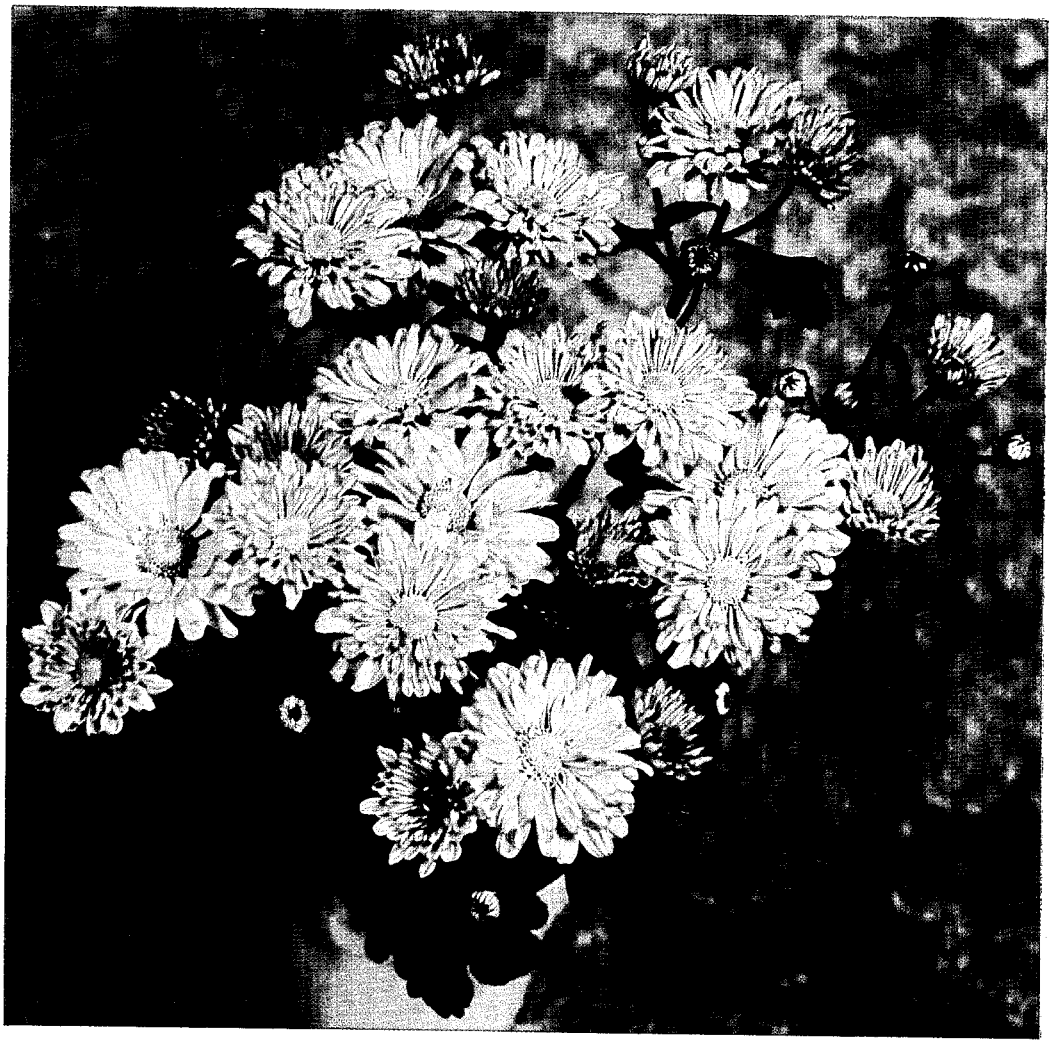

CHRYSANTHEMUM PLANT
Filed July 10, 1972 2 Sheets-Sheet 2
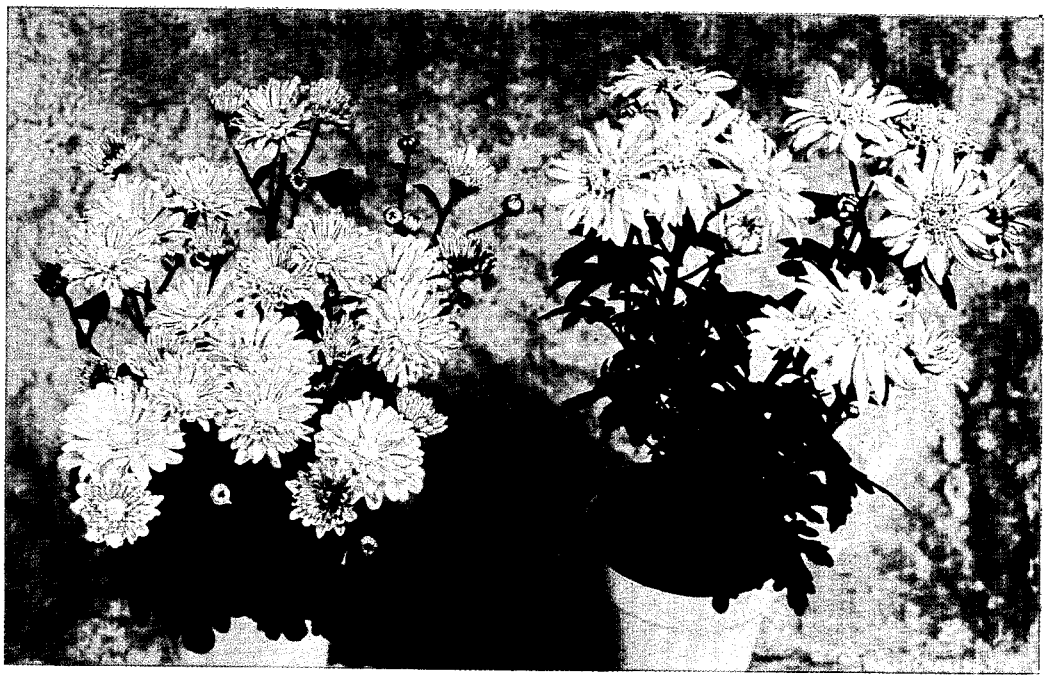

United States Patent Office

Plant Pat. 3,530

Patented Mar. 19, 1974

3,530
CHRYSANTHEMUM PLANT

Grace H. Mack, 108 Wahackne Road, New Canaan, Conn. 06840, and Walter H. Jessel, Jr., Doylestown, and William E. Duffett, Akron, Ohio; said Jessel and Duffett assignors to said Mack

Filed July 10, 1972, Ser. No. 269,943

Int. Cl. A01h *5/00*

U.S. Cl. Plt.—74 1 Claim

The present invention comprises a new and distinct cultivar of chrysanthemum plant which is a seedling of Preview × #C102–66. Both parents are unpatented and the numbered parent is identified for breeding purposes in this manner.

The new cultivar is similar in many respects to the unpatented cultivar Tango, having the same characteristics of:

(1) Use as a garden chrysanthemum.

(2) A similar period of value.

(3) A medium to light lavender flower color with good color retention.

(4) A wide spreading habit.

The new cultivar is also similar in many respects to the unpatented cultivar Mischief, having the same characteristics of:

(1) Use as a garden chrysanthemum.

(2) A daisy flower form.

(3) A similar period of value.

The new cultivar is distinguished from Tango by the following characteristics when grown under comparable conditions:

(1) Flowers approximately ¾″ smaller in diameter.

(2) A daisy or single form rather than an anemone form.

(3) A lighter foliage color.

(4) An earlier natural season flowering date. It flowers approximately September 25 compared to approximately October 8 for Tango.

(5) A more compact habit with approximately three inches less vigor.

The new cultivar is distinguished from Mischief by the following characteristics when grown under comparable conditions:

(1) Flowers are approximately ¼″ larger in diameter.

(2) An earlier natural season date. It flowers approximately September 25 compared to approximately October 12 for Mischief.

(3) A much lighter pink color with better color retention.

(4) A smaller disc (perfect florets).

(5) Approximately 3″ shorter habit.

(6) A lighter foliage color.

(7) Less prominent stipules.

(8) Approximately 3–4 days more keeping quality.

The new cultivar was selected from the progeny of the designated cross and when asexually reproduced by cuttings at Barberton, Ohio, has been found to retain its distinctive characteristics through successive propagations.

The new cultivar when grown in the vicinity of Barberton, Ohio, has a response period of approximately 7 weeks, and the following detailed description is based on observations made of the new cultivar in a greenhouse in Barberton, Ohio. The response time, blooming period, color and total vigor may vary significantly with varying environmental conditions such as temperature, daylength, and light intensity. Suggested flowering in the northern and western United States is from April through May and September through October; in Florida, January through February.

The accompanying drawings show the unique characteristics of the new cultivar, the color being as nearly true as possible with color illustrations of this type. Sheet 1 comprises a color photograph of the new cultivar by itelf, and Sheet 2 comprises a comparison color photograph, with the new cultivar appearing on the left and the comparison cultivar Tango on the right. In the description which follows, color references are made to the Munsell Color Book, 1963 edition, and comparisons are made with the cultivars Tango and Mischief. Where only a single value or description appears for new cultivar Stardom, the same value applies as well to the comparison cultivars.

Botanical classification: *Chrysanthemum morifolium*

| | Stardom | Tango | Mischief |
|---|---|---|---|
| Bloom: | | | |
| Size | 1¾″ | 2½″ | 1″. |
| Fully expanded | 2¼″ | 3″ | 1½″. |
| Borne | Clusters on elongated pedicels | | |
| Stems | Wiry | | |
| Form | Daisy | Anemone | Daisy. |
| Permanence | 10–14 days | 10–14 days | 7–10 days. |
| Color: | | | |
| Center of flower | Yellow green, 8.75Y7/12 to dark yellow, 1.25Y7/4. | Greyed yellow, 5Y7/8 | Dark yellow, 1.25Y7/14. |
| Base of petals | Yellow green, 2.5GY8/10 | Yellow green, 2.5GY7/10 | White, N95/. |
| Inside of petals | Greyed lavender, 2.5RP5/8 to lavender, 10P6/8. | Greyed lavender, 2.5RP5/8 to lavender, 10P7/6. | Purple, 7.5RP3/10 to dark lavender, 2.5RP5/10. |
| Reverse of petals | Lavender, 10P7/6 over light lavender, 10P8/4. | Greyed lavender, 10P6/8 over light lavender, 10P8/4. | Dark lavender, 2.5RP5/10. |
| Tonality from a distance. | Light lavender | Light lavender | Purple. |
| Discoloration | Light greyed lavender, 10P8/4 | Greyed lavender, 2.5RP6/6 over light lavender, 10P8/4. | Dark lavender, 2.5RP5/10. |
| Petals: | | | |
| Texture | Smooth | | |
| Appearance and form | Closed at base, broadening rapidly to a wide, flat keel, tapering quickly to a notched rounded tip. | Open at base, flaring quickly to a flat keel with occasional reverse petal edge roll, tapering to a deeply notched sharp tip. | Open at base, shallow broad keel tapering quickly to a blunt notched point. |
| Arrangement | Composite, whorled on a single receptacle. | | |
| Persistence | Resist shatter | | |
| Fragrance | Typical chrysanthemum | | |
| Reproductive organs: | | | |
| Stamen, anthers | 150–200 | 200–250 | 200–250. |
| Pollen | None to abundant (functional sterility). | | |
| Arrangement | Clustered in center of flower, if present. | | |
| Styles | Present both ray and disc florets | | |
| Length | Short | | |
| Ovaries | At the base of petal attached to receptable. | | |

Botanical classification: *Chrysanthemum morifolium*—Continued

| | Stardom | Tango | Mischief |
|---|---|---|---|
| Plant: | | | |
| Form | Herbaceous | | |
| Growth | Compact spreading | Spreading | Compact spreading. |
| Height | Approximately 11″ when flowered naturally as field grown plants from a planting made in mid-June and given a single pinch in late June. | Approximately 14″ when flowered naturally as field grown plants from a planting made in mid-June and given a single pinch in late June. | Approximately 14″ when flowered naturally as field grown plants from a planting made in mid-June and given a single pinch in late June. |
| Spread | Approximately 12″ when flowered naturally as field grown plants from a planting made in mid-June and given a single pinch in late June. | | |
| Foliage: | | | |
| Top side | Dark green, 7.5GY4/4 | Very dark green, 7.5GY3/4 | Very dark green, 7.5GY3/4. |
| Size | 3¼″ long, 2″ wide | 3½″ long, 1¾″ wide | 3″ long, 1¾″ wide. |
| Quantity | Numerous | | |
| Shape | Spatulate lobed | | |
| Texture | Coarse | | |
| Ribs and veins | Prominent | | |
| Edge | Moderately indented | | |
| Serration | Moderate | Slight | Moderate. |
| Under side | Light green, 7.5GY5/4 | | |
| Stipules | Rudimentary | Rudimentary | Prominent. |

We claim:

1. A new and distinct cultivar of chrysanthemum characterized particularly as to its uniqueness when compared to the cultivar Tango by its flowers which are approximately ¾″ smaller in diameter; its daisy or single form rather than an anemone form; lighter foliage color; an earlier natural season flowering date, flowering from approximately Sept. 25 compared to approximately Oct. 8 for Tango, and by its more compact habit with approximate three inches less vigor; and characterized particularly as to its uniqueness when compared to the cultivar Mischief by its flowers which are approximately ¼″ larger in diameter; an earlier natural season date, flowering approximately Sept. 25 as compared to approximately Oct. 12 for Mischief; its much lighter pink color with better color retention; a smaller disc providing perfect florets; approximately 3″ shorter habit; lighter foliage color; less prominent stipules, and its approximately 3–4 days longer keeping quality.

No references cited.

ROBERT E. BAGWILL, Primary Examiner

UNITED STATES PATENT OFFICE
CERTIFICATE OF CORRECTION

Patent No. PP-3530 Dated March 19, 1974

Inventor(s) GRACE H. MACK, WALTER H. JESSEL, JR. and WILLIAM E. DUFFETT

It is certified that error appears in the above-identified patent and that said Letters Patent are hereby corrected as shown below:

In the tabulated description below Columns 1 and 2, below "Color:" and opposite "Base of petals", under "Mischief" change "White, N95/." to --White, N9.5/.--.

Signed and sealed this 17th day of September 1974.

(SEAL)
Attest:

McCOY M. GIBSON JR.
Attesting Officer

C. MARSHALL DANN
Commissioner of Patents

USCOMM-DC
U.S. GOVERNMENT PRINTING OFFICE